United States Patent
Racenet et al.

(10) Patent No.: US 9,622,765 B2
(45) Date of Patent: Apr. 18, 2017

(54) VACUUM ASSISTED SURGICAL DISSECTION TOOLS

(75) Inventors: Danyel J. Racenet, Middletown, CT (US); Timothy N. Wells, Manchester, CT (US); Steven L. Bennett, Cheshire, CT (US); Amin Elachchabi, Hamden, CT (US); Michael J. Bettuchi, Middletown, CT (US); Miles William Noel Hember, Cambridge (GB)

(73) Assignee: Covidien LP, Mansfield, MA (US)

( * ) Notice: Subject to any disclaimer, the term of this patent is extended or adjusted under 35 U.S.C. 154(b) by 709 days.

(21) Appl. No.: 12/579,296

(22) Filed: Oct. 14, 2009

(65) Prior Publication Data

US 2010/0256662 A1 Oct. 7, 2010

Related U.S. Application Data

(60) Provisional application No. 61/107,752, filed on Oct. 23, 2008.

(51) Int. Cl.
| | |
|---|---|
| *A61B 17/32* | (2006.01) |
| *A61B 10/06* | (2006.01) |
| *A61B 17/30* | (2006.01) |

(52) U.S. Cl.
CPC ...... *A61B 17/320016* (2013.01); *A61B 10/06* (2013.01); *A61B 2017/308* (2013.01); *A61B 2017/32004* (2013.01)

(58) Field of Classification Search
CPC .............. A61B 10/06; A61B 2017/308; A61B 2017/32004

USPC ........ 606/106, 107, 110, 114, 115, 127, 159, 606/167–180; 600/562, 565; 604/22, 44
See application file for complete search history.

(56) References Cited

U.S. PATENT DOCUMENTS

| | | | | |
|---|---|---|---|---|
| 1,847,328 | A | * | 3/1932 | Berzon ................. A47J 43/282 425/285 |
| 2,155,700 | A | * | 4/1939 | Donahue ............... A47J 43/282 425/187 |
| 5,437,630 | A | | 8/1995 | Daniel et al. |
| 5,468,247 | A | | 11/1995 | Matthai et al. |
| 5,669,921 | A | * | 9/1997 | Berman et al. ............... 606/167 |
| 5,702,360 | A | | 12/1997 | Dieras et al. |
| 5,766,198 | A | | 6/1998 | Li |
| 5,823,971 | A | * | 10/1998 | Robinson et al. ............ 600/567 |
| 5,957,881 | A | | 9/1999 | Peters et al. |
| 6,010,477 | A | | 1/2000 | Bays |
| 6,068,603 | A | * | 5/2000 | Suzuki ............................ 600/565 |
| 6,090,041 | A | | 7/2000 | Clark et al. |
| 6,342,061 | B1 | | 1/2002 | Kauker et al. |
| 6,468,286 | B2 | * | 10/2002 | Mastri et al. .................. 606/169 |
| 6,620,180 | B1 | * | 9/2003 | Bays et al. ..................... 606/171 |
| 6,641,575 | B1 | * | 11/2003 | Lonky ............................ 604/540 |
| 6,840,948 | B2 | * | 1/2005 | Albrecht et al. .............. 606/170 |
| 6,955,676 | B2 | * | 10/2005 | Quick ............................. 606/45 |
| 7,179,224 | B2 | | 2/2007 | Willis |
| 7,303,559 | B2 | | 12/2007 | Peng et al. |

(Continued)

*Primary Examiner* — Gregory Anderson
*Assistant Examiner* — Sarah Simpson

(57) ABSTRACT

A surgical device comprising a handle, an elongated tube extending distally from the handle, and a suction tip at a distal end portion of the elongated tube. The suction tip has a cavity formed therein. A cutting blade is positioned at least partially within the cavity and rotatable across the cavity to sever tissue, the cavity dimensioned to receive the severed tissue for removal from a patient's body.

26 Claims, 8 Drawing Sheets

(56) References Cited

U.S. PATENT DOCUMENTS

| | | |
|---|---|---|
| 7,473,263 B2 | 1/2009 | Johnston et al. |
| 7,485,090 B2 | 2/2009 | Taylor |
| 2004/0181239 A1* | 9/2004 | Dorn et al. .................. 606/108 |
| 2004/0181248 A1 | 9/2004 | Josephson |
| 2006/0047219 A1* | 3/2006 | Baruti et al. .................. 600/564 |
| 2008/0103412 A1* | 5/2008 | Chin .............................. 600/566 |
| 2010/0016786 A1* | 1/2010 | Drews et al. .................. 604/22 |

* cited by examiner

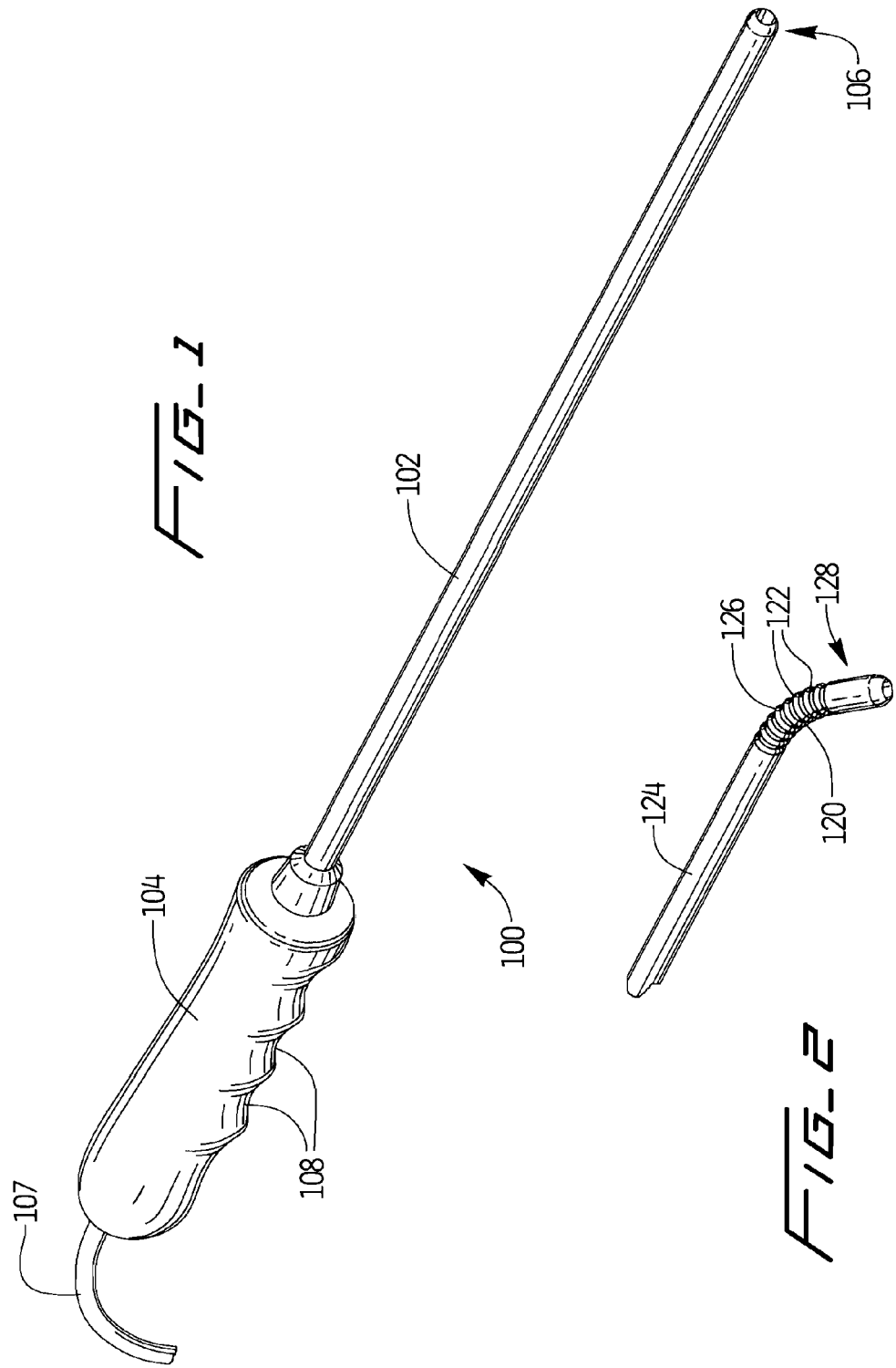

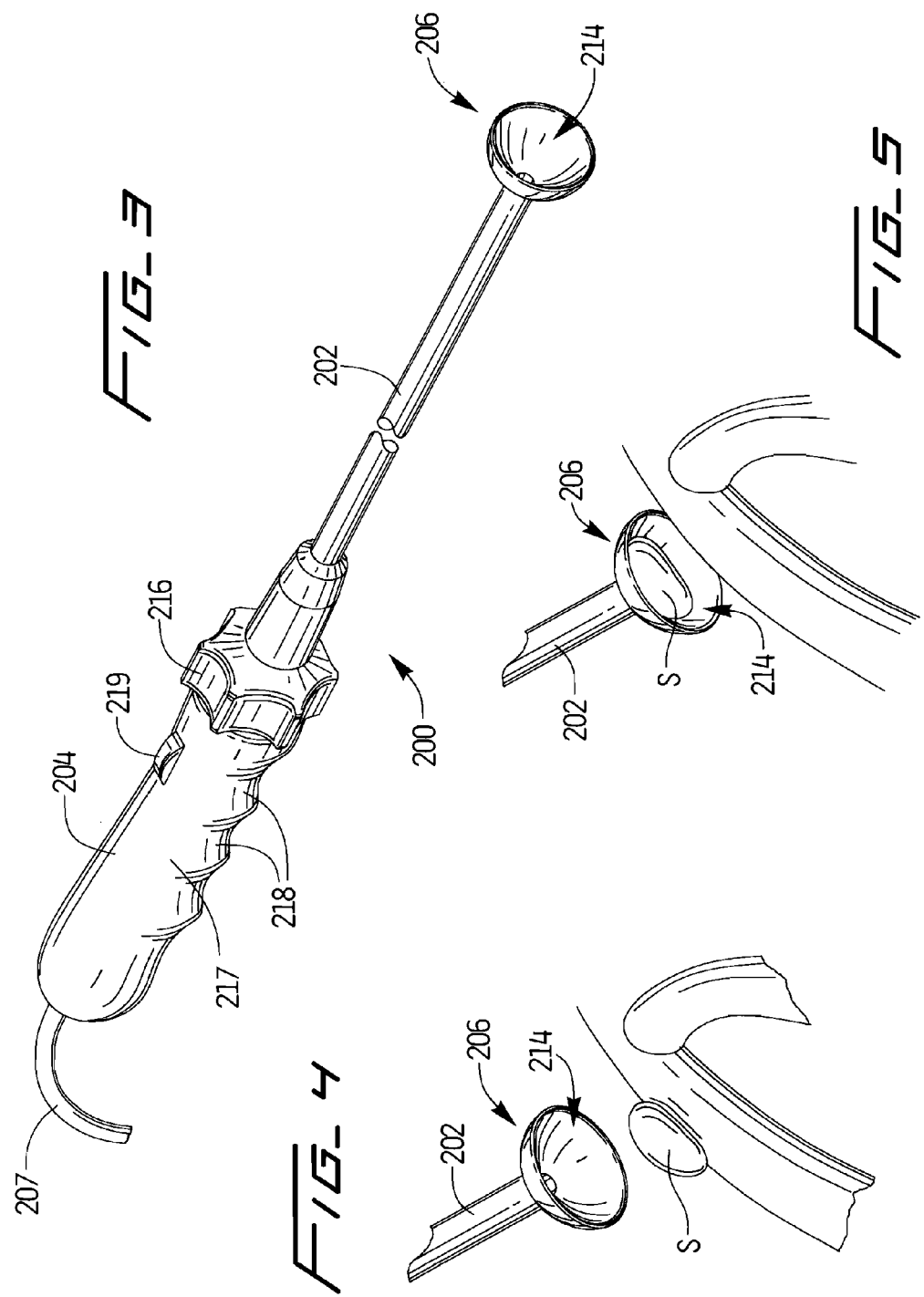

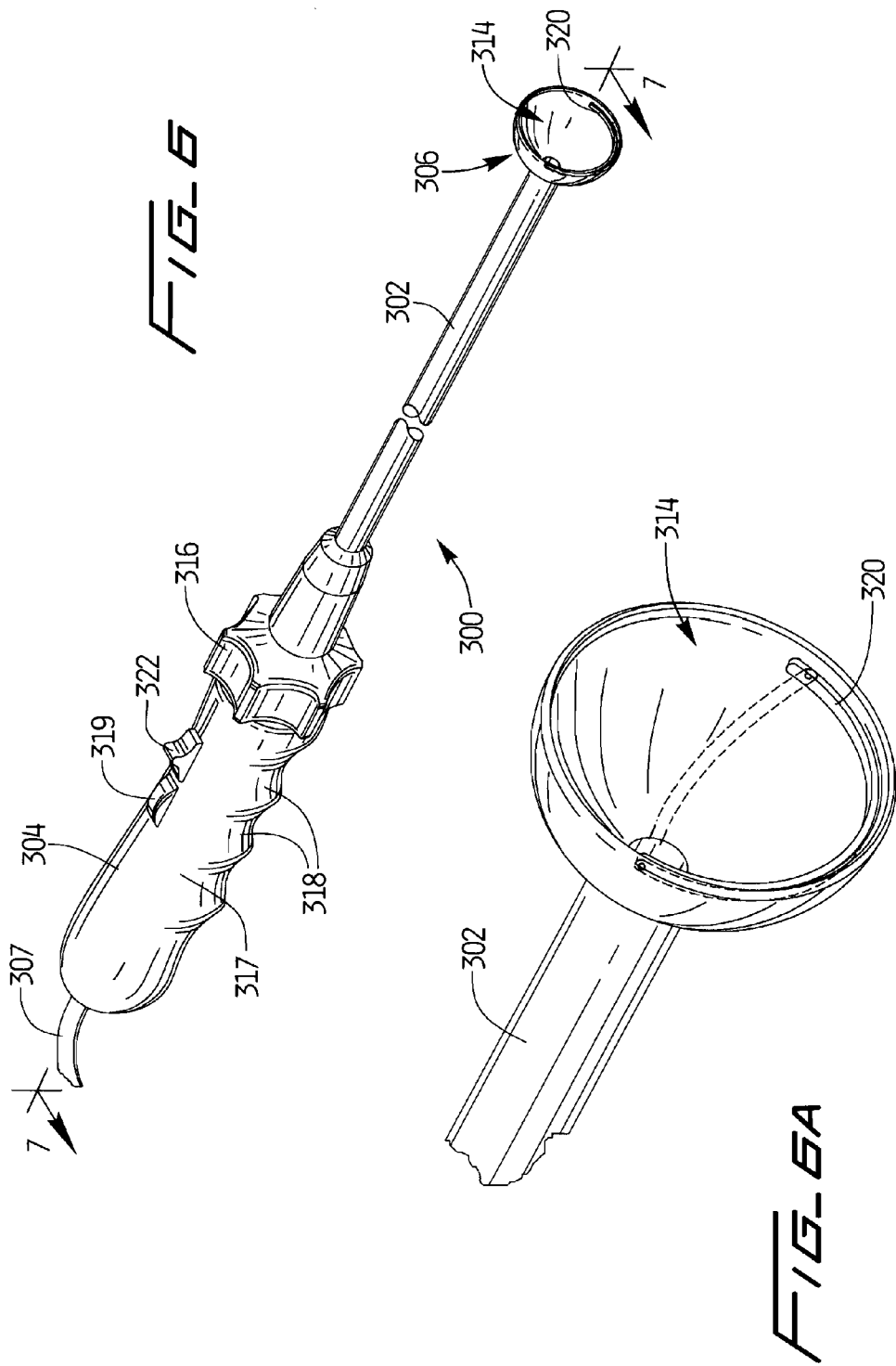

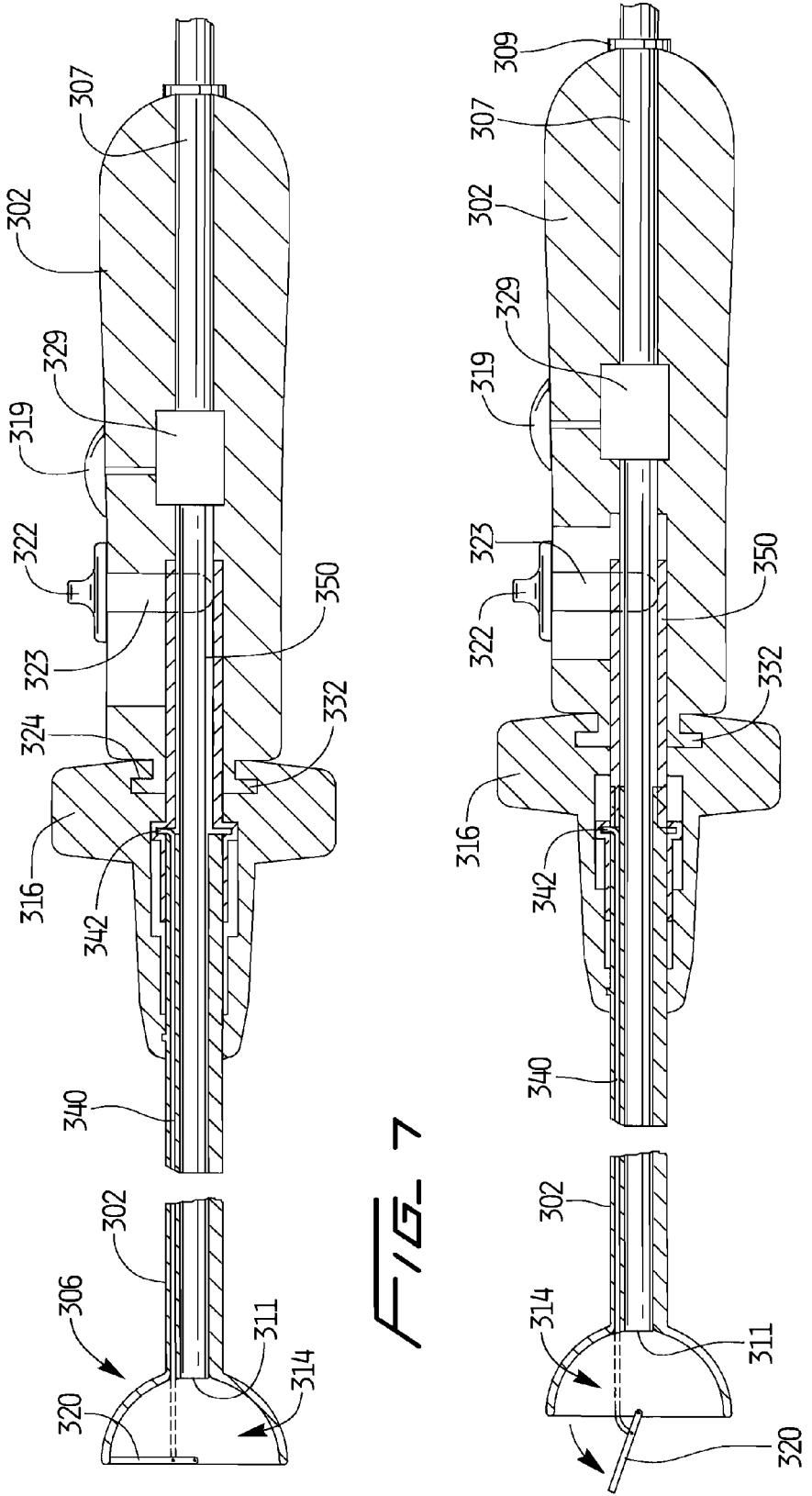

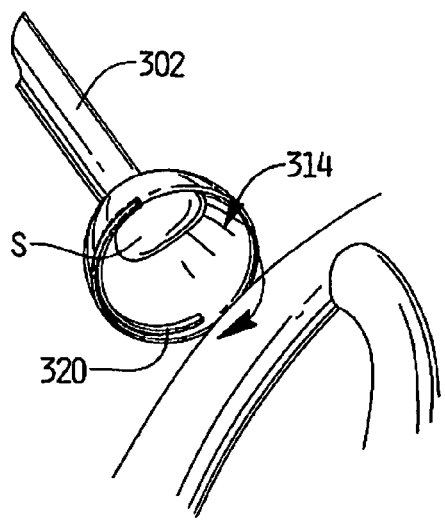
FIG_11
FIG_12
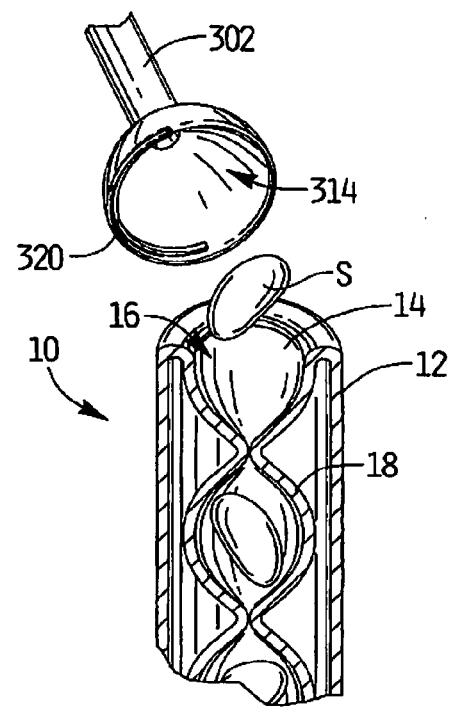

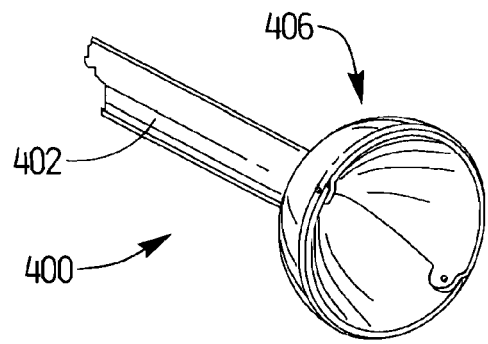
FIG_13
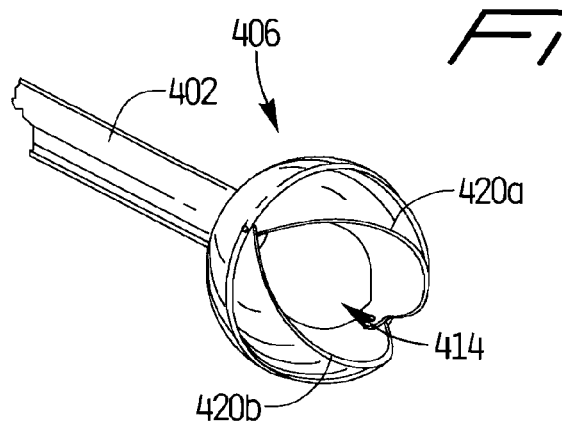
FIG_14
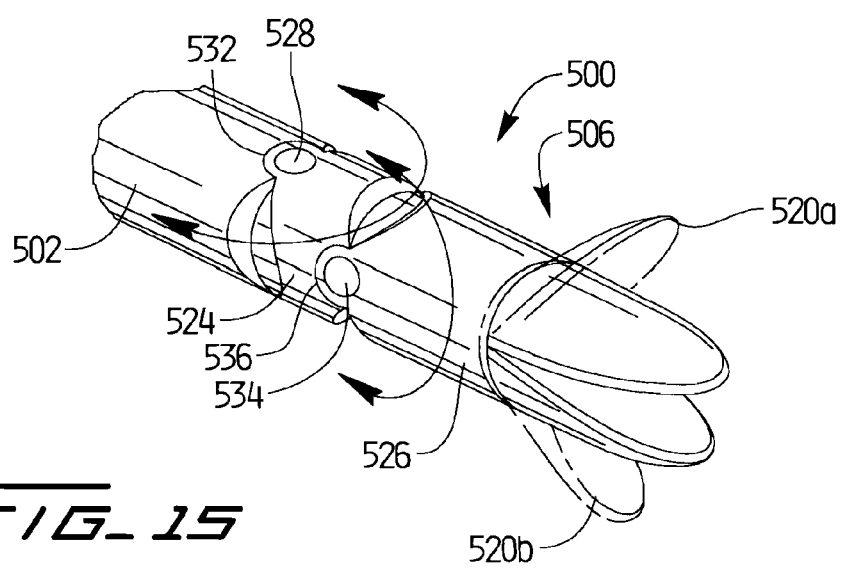
FIG_15

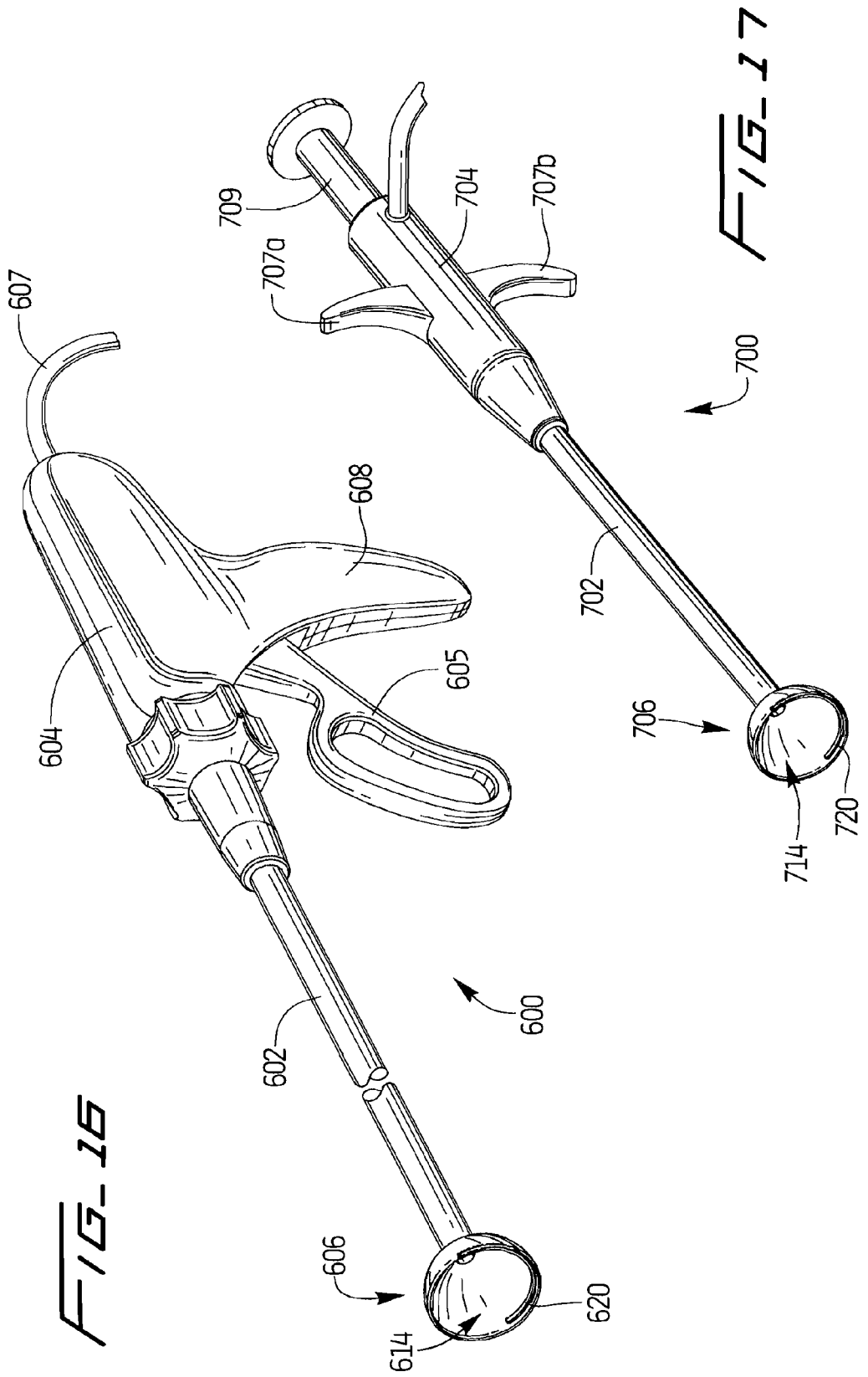

VACUUM ASSISTED SURGICAL DISSECTION TOOLS

This application claims priority from U.S. Provisional Application No. 61/107,752, filed Oct. 23, 2008, the entire contents of which are incorporated herein by reference.

BACKGROUND

Technical Field

This application relates to a device for minimally invasive surgery and more particularly to a vacuum device for minimally invasive thoracic surgery.

Description of the Related Art

In recent years, new methods of access into the thoracic cavity have been developed in order to perform some of the surgical procedures done before through a median sternotomy. One minimally invasive method is called a mini-thoracotomy and involves access through an incision running intercostally (between two ribs) of the left chest wall. A surgical retractor is used as for the median sternotomy, but in this case, the superior and inferior rib cages of the left chest are spread apart about two inches, thus resulting in much less overall trauma to the bones, muscles, and other tissues in the chest. Subsequently, the patient endures less pain and irritation following the surgery and the recovery time is significantly decreased.

The mini-thoracotomy method of access to the thoracic cavity, however, has propagated the need for new surgical tools and methods because the opening into the thoracic cavity is considerably smaller than for the sternotomy. Also, since the internal mammary arteries are attached to the thoracic cavity wall, the angle of approach the surgeon must use through the opening is very difficult since the inferior rib cage tends to obstruct the manipulation of surgical devices used for the procedure.

During thoracic surgery, cancerous tumors may need to be removed. The need exists for instrumentation for such surgery to easily remove the tumors while avoiding seeding.

SUMMARY

The present disclosure provides a surgical device comprising a handle, an elongated tube extending distally from the handle, and a suction tip at a distal end portion of the elongated tube. The suction tip has a cavity formed therein and vacuum tube communicates with the suction tube to aspirate a tissue section. A cutting blade is positioned at least partially within the cavity and rotatable across the cavity to sever the tissue section, wherein the cavity is dimensioned to receive the severed tissue section for removal from a patient's body.

In one embodiment, the cutting blade has an arcuate surface.

Preferably, the handle includes a manual member for rotating the blade across the cavity. The manual member is preferably operatively connected to an elongated actuator and the actuator is operatively connected to the blade. In one embodiment, sliding movement of the manual member moves the actuator to rotate the cutting blade. In another embodiment, pivotal movement of the manual member moves the actuator to rotate the cutting blade. In an alternate embodiment, the manual member includes a plunger.

The handle can include a switch for activating and shutting the vacuum.

The blade in one embodiment can rotate across the cavity in an arc of about 180 degrees. In one embodiment, in an undeployed position, the blade remains within the confines of the cavity and in the deployed position, at least a portion of the blade extends beyond the confines of the cavity.

BRIEF DESCRIPTION OF THE DRAWINGS

Various embodiments of the present disclosure are described hereinbelow with reference to the drawings, wherein FIG. 1 is a perspective view of a first embodiment of a surgical device of the present disclosure;

FIG. 2 is a perspective view of an alternate embodiment of the device of FIG. 1;

FIG. 3 is a perspective view of another embodiment of the surgical device of the present disclosure;

FIG. 4 is a perspective view illustrating the device of FIG. 1 approaching a specimen for removal;

FIG. 5 is a view similar to FIG. 4 illustrating the specimen being removed by the device of FIG. 3;

FIG. 6 is a perspective view of another embodiment of the surgical device of the present disclosure showing the blade in a first (undeployed) position;

FIG. 6A is a close up view of the distal portion of the device of FIG. 6;

FIG. 7 is a longitudinal cross-sectional view taken along line 7-7 of FIG. 6 with the cutting blade in the initial position;

FIG. 9 is a longitudinal cross-sectional view similar to FIG. 7 showing the blade in the deployed position corresponding to the position of FIG. 8;

FIG. 11 is a view similar to FIG. 10 illustrating retraction of the blade to its initial position and removal of the specimen;

FIG. 12 illustrates a container for receiving the specimen;

FIG. 13 is a perspective view of an alternate embodiment of the present disclosure showing the blades in the closed position;

FIG. 14 is a perspective view similar to FIG. 13 showing the blades in the open position;

FIG. 15 is a perspective view showing articulation of the distal portion of an alternate embodiment of the device of the present disclosure; and FIGS. 16 and 17 are perspective views of alternate embodiments of the present disclosure having different handle mechanisms for deploying the cutting blade.

DETAILED DESCRIPTION OF THE EMBODIMENTS

Figures 8, 10:
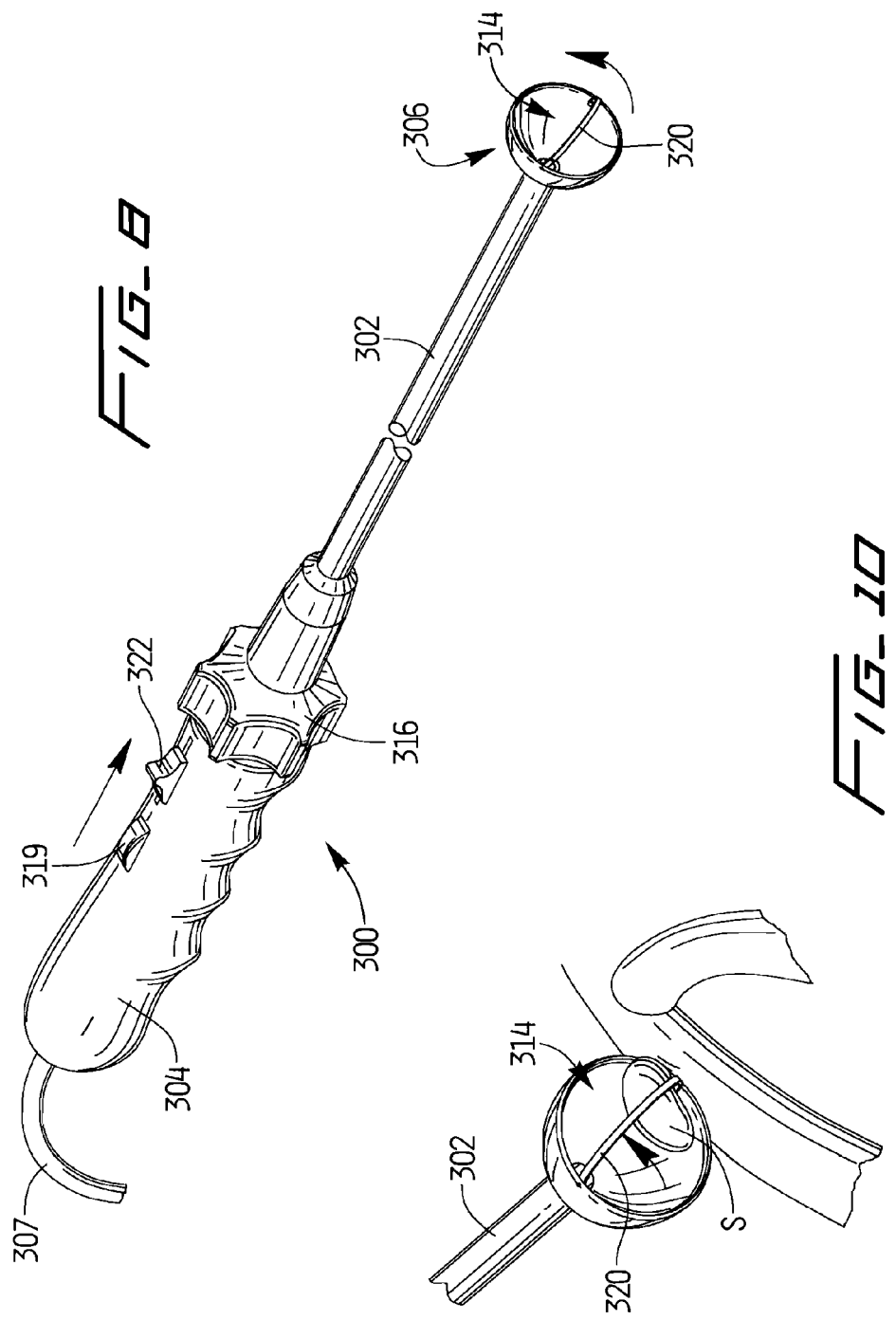
FIG. 8 is a perspective view of the device of FIG. 6 showing the blade in the second (deployed) position.
FIG. 10 is a close up view of the distal portion of the device of FIG. 8 showing movement of the cutting blade to sever tissue for removal of a specimen.

The present disclosure relates to vacuum assisted devices. In some embodiments, the vacuum is used for dissection and specimen retrieval, such as in FIGS. 1-5. These suction devices enable a surgeon to have controlled tension during delicate dissection. In other embodiments, a cutting blade is used to sever the tissue adjacent the specimen and a vacuum is used for specimen retrieval, such as in FIGS. 6-17.

FIG. 1 illustrates a first embodiment of the device of the present disclosure, designated generally by reference numeral 100. Device 100 has an elongate tube or shaft 102 and a handle 104 attached at the proximal end thereof. The elongate tube 102 has a suction tip 106 disposed on the distal end. A vacuum tube 107 extends from the proximal end of the handle 104. The handle can have indentations 108 to enhance gripping by the clinician. The suction tip 106 is configured and dimensioned to vacuum a tumor specimen into the distal end thereof. This embodiment enables a surgeon to intercostally enter the thoracic region through an access port such as a thoracoport used in minimally invasive thoracic surgery. After the surgeon identifies a specimen, application of the device allows the surgeon to vacuum the specimen up into the suction tip 106 and remove the specimen through the access port. The specimen in this embodiment, as well as other embodiments disclosed herein, can be suctioned through a lumen in the elongated tube 102 or sufficient vacuum can hold the specimen at the tip 106 during removal of the instrument from the body through the access port.

The elongated tube 102 is shown as substantially straight and substantially rigid. Alternatively the device can be provided with a flexible or articulating region such as shown in the embodiment of FIG. 2. In this embodiment, elongated tube 124 has a flexible region 126 which enhances the maneuverability of the device as tip 128 can be angled with respect to the other portions of tube 124. A vacuum would be applied through elongated tube 124. The articulating region 126 can in one embodiment include a plurality of vertebral members sandwiching a plurality of disks 122, each of the plurality of disks 122 disposed between adjacent vertebral members 120 along the longitudinal axis, wherein the articulating region 126 enables angular articulation of the suction tip 106. The articulation can be achieved by manipulation of a proximal control (not shown) at a proximal end of the tool. Alternatively, the articulation can be achieved by applying a force directly to the articulation region.

FIGS. 3-5 illustrate an alternate embodiment of the suction instrument. Device 200 has an elongate member or tube 202, a handle 204, and a suction end 206 at the distal end of tube 202. The suction end 206 has a substantially hemispherical shape forming a substantially hemispherical shaped cavity 214 dimensioned to receive and hold a specimen. The housing or handle 204 has a rotation knob 216 and a gripping portion 217 with indentations 218 to enhance gripping of the device 200 by the clinician. Vacuum tube 207, extending from housing 204, communicates with the lumen of tube (shaft) 202 to apply a vacuum to the suction tip 206. Handle 204 also includes a switch 219 to turn the vacuum on and off. The knob 216 is configured and dimensioned to rotate the elongate tube 204 and suction tip 206 about the longitudinal axis of the tube 204. A porous membrane (not shown) can be provided in this and other embodiments which spans the cavity to limit bypass flow. In use, as shown in FIGS. 4 and 5, the suction tip 206 is applied to specimen S and the vacuum suctions the specimen S into the cup shaped cavity 214 to enhance retention of the specimen for removal through an access port. The specimen can also be suctioned through tube 202.

In the embodiment of FIGS. 6-12, the device 300 is similar to device 200 of FIG. 3, except for the provision of a cutting blade to sever the tissue adjacent the specimen to separate the specimen for removal and pathology. Device 300 has an elongate member or tube 302 extending from housing or handle 304 and a suction tip 306 at a distal end of tube 302. Gripping portion 317 of handle 304 has indentations 318 to enhance gripping by the clinician.

The suction tip 306 has a substantially hemispherical shape forming a substantially hemispherical shaped cavity 314 dimensioned to receive and hold a specimen. The handle 304 has a rotation knob 316 to rotate the elongate tube 304 and the attached suction tip 306 about the longitudinal axis of the tube 304. As shown in FIG. 7, projection 332 of housing 304 engages notch or recess 324 of knob 316 to fix the knob 316 axially but allow rotational movement about its axis. The knob 316 is connected to the shaft 304 to enable the shaft 304 and the suction tip 306 to be rotated should the surgeon need to dissect tissue at alternative angles within a 360 degree rotation. Thus, rotation of the knob 316 facilitates a plurality of cutting angles for the cutting blade 320.

Vacuum tube 307 extends through the housing 304 and through the lumen of tube (shaft) 304, terminating at opening 311 adjacent the cavity 314, to apply a vacuum to the suction tip 306. The tube 307 includes an O-ring seal 309. Handle 304 also includes an on/off switch 319 for the vacuum. The switch 319 can be configured to open and close a valve, shown schematically and labeled with reference numeral 329.

A cutting blade 320 with an outer cutting edge is supported within cavity 314 and is rotatable across the cavity to various positions with respect to the opening of cavity 314 to sever tissue. In a preferred embodiment, this "wiper" blade 320 is configured and dimensioned to rotate across an arc of about 180 degrees, although other degrees of rotation are also contemplated. The blade 320 is connected to a rod or wire 340 (or other elongated actuator) which extends within a lumen in the tube 304 as shown in FIGS. 7 and 9. The lumen is adjacent and parallel to the lumen of the tube 304 which receives the vacuum tube 307. The proximal end of rod 340 has a flange 342 which is seated within a recess in connector tube 350. At the proximal end of connector tube 350, an opening is formed to receive projecting portion 323 of slide knob 322 to operably connect the knob 322 to the connecting tube 350. In this manner, blade 320 is operably connected to the slide knob 322 as slide knob 322 on housing 304 slides to rotate the cutting blade 320 across the cavity 314. That is, the knob 322 is configured to rotate the blade 320 and is operatively connected to elongated rod 340 (or a wire) which in turn is operatively connected to the blade 320. The blade 320 is configured and dimensioned to laterally dissect extraneous tissue attached to the specimen S, readily enabling intact removal of specimen S for pathology.

FIGS. 6 and 7 illustrate the cutting blade 320 in its initial position, positioned within the confines of the cavity 314 of suction tip 306. In this position, slide knob 322 and connector tube 350 (and actuation rod 340) are in the retracted (proximal) position. To deploy the cutting blade so it rotates in an arc across the cavity as shown in FIGS. 6A, 8 and 9, knob 322 is slid distally to advance connector tube 350 which in turn advances attached actuation rod 340. Such distal movement of actuation rod 340 rotates the blade in the direction of the arrow of FIGS. 5 and 9.

As shown in FIGS. 10 and 11, the suction tip 306 is applied to the severed specimen S and the vacuum suctions the specimen into the cup shaped cavity 314 to enhance retention of the specimen for removal through an access port. The specimen can be held in cavity 314 for removal or suctioned into the device through the vacuum tube 307.

Use of the device 300 will now be described. The instrument 300 is inserted through an access port adjacent the specimen S. The blade 322 is in the undeployed position within the confines of the cavity 314 (FIGS. 6, 6A) and adjacent a wall of the cavity 314. Slide knob 322 is then actuated (slid distally) in the direction of the arrow (FIG. 8), causing rod (or wire) 340 to move distally to rotate the blade across the cavity 314 in the direction of the arrow of FIG. 10. Full rotation to the opposite wall of the cavity 314 (in an arc of about 180 degrees) severs the specimen S from surrounding tissue and the vacuum force suctions it into the cavity 314 where it is securely held. The blade 322 is then returned to its initial position (see arrow of FIG. 11) by retraction of the slide knob 322 which retracts rod 340 to the initial position of FIG. 6. The device 300 is withdrawn from the body cavity and access port and the specimen S can then be released into a container 400 (FIG. 12) by terminating the vacuum.

FIGS. 13-14 illustrate another embodiment of the suction device of the present disclosure. Device 400 (only the distal end portion is shown) comprises an elongate member 402 having a suction tip 406. Suction tip 406 has a substantially spherical shape and a cavity 414 disposed in the distal end thereof. The suction tip 406 has first and second cutting blades 420a, 420b, pivotably connected in mirror image arrangement to the distal end of the suction tip 406, and each part of a substantially hemispherical cup. Each blade 420a, 420b is configured and dimensioned to rotatably engage about a plane disposed in longitudinal alignment with the elongate member 402. A handle similar to handle 304 of FIG. 6 can be provided which has a rotatable knob, a slide knob and a switch similar to knobs 316, 319 and switch 322, such that the knob is configured and dimensioned to rotate the elongate member 402 and suction tip 406 about the longitudinal axis, a switch is configured and dimensioned to turn the vacuum on and off, and a knob is configured and dimensioned to rotate the first and second blades 420a, 420b between a closed position of FIG. 13 and an open position of FIG. 14. The knob enables the suction tip 406 to be rotated so that should the surgeon need to dissect tissue at alternative angles within a 360 degree rotation, rotation or articulation of the knob facilitates a plurality of cutting angles.

In use, the device 400 is inserted through an access port, e.g. a thoracoport, with the blades in the closed position closing the cavity 414 and presenting to tissue an atraumatic spherical end surface. Note that alternatively, the device 400 can be inserted with the blades 420a, 420b in the open position of FIG. 14. If inserted in the closed position of FIG. 14, once inside the body cavity and past the distal end of the access port, the blades are moved to the open position, separated from another and opening the cavity 314. The blades 420a, 420b (and "cups") are then moved toward each other to laterally dissect extraneous tissue, and allowing the specimen to be captured within cavity 314. The vacuum helps to retain the specimen inside the cavity 414. The cup shaped members remain in the closed position to encapsulate the specimen S for removal.

In the embodiment of FIG. 15, device 500 (only the distal portion is shown) has an elongate member 502 having a first post 524, a second post 526, and a suction tip 506. The first post 524 is pivotably attached to the distal end of the elongate member 502 by a first pin 528 disposed through a transverse bore of the elongate member 502 and through a clevis 532 on the proximal portion of the first post 524. The second post 526 is pivotably connected to the first post 524 by a second pin 534 disposed through a transverse bore disposed on the distal end of the first post 524 and through a second clevis 536 disposed on the proximal end of the second post 526. The suction tip 506 has first and second blades 520a, 520b pivotably connected in mirror image at the distal end of the suction tip 506, wherein each blade 520a, 520b is configured and dimensioned to rotatably engage about a plane disposed in longitudinal alignment with the elongate member 502.

A handle similar to handle 304 of the embodiment of FIG. 4 has a rotatable knob, a slidable knob, and an on/off vacuum switch similar to knobs 316, 322 and switch 319 of FIG. 4. The rotation knob is configured and dimensioned to rotate the elongate member 502 and suction tip 506 about the longitudinal axis should the surgeon need to dissect tissue at alternative angles within a 360 degree rotation. The sliding knob rotates (articulate) the blades 520a, 520b, between open and closed positions.

Each of the first and second posts 524, 526 can be controlled by a second or third switch, lever, or other mechanism for articulating the suction tip 506 to engage specimens at various angles. The second post 526 is configured and dimensioned to articulate in the direction of the arrow, e.g. upward and downward as viewed in the orientation of FIG. 15, and the first post 524 is configured and dimensioned to articulate in a different direction (see arrow of FIG. 15), e.g. side to side rotation in the orientation of FIG. 15. Note that each post 524, 526 can be configured and dimensioned to articulate in the others articulation direction.

In this embodiment, the blades 520a, 520b are configured to laterally dissect extraneous tissue attached to the specimen S, readily enabling removal of the specimen, in a similar manner as described for devices 300, 400 of FIGS. 6-12, 13-14, respectively.

In the embodiment of FIG. 16, device 600 has an elongate tube or shaft 602 and a handle 604 attached at the proximal end thereof, the elongate tube 602 having a suction tip 606 disposed on the distal end. A vacuum tube 607 extends from the proximal end of the handle 604. This embodiment is similar to the embodiment of FIG. 6, except that instead of a sliding knob to deploy the blade, a pivotable trigger 605 is provided. The trigger 605 is operably connected to an elongated wire or rod (or other elongated member) which is operably connected to blade 620. Proximal movement of trigger 605 toward stationary handle 608 moves the rod distally to pivot the blade 620 across the cavity 614 in the same manner as blade 320 described above. The suction tip 606 is configured and dimensioned to vacuum a tumor specimen into the distal end thereof. Vacuum tube 607 can be used to retain the severed specimen in the cavity 614 or to aspirate it through the device 600.

The device 700 of FIG. 17 is identical to the device 300 of FIG. 6 except instead of a sliding knob to rotate the blade, a syringe type pusher is provided. The handle 704 includes wings 707a, 707b extending transversely therefrom for gripping by the clinician. Shaft 702 extends distally from the housing 704. Pusher or plunger 709 is operably connected to a rod or wire (or other elongated member) which is operably connected to blade 720. Actuation of plunger 709, e.g. distal movement, advances the rod or wire to rotate the blade 720 across cavity 714 of suction tip 706 in the same manner as blade 320 of the embodiment of FIG. 6. Vacuum tube 707 can be used to retain the severed specimen in the cavity 714 or to aspirate it through the device 700.

In the embodiments described herein, instead of a cutting blade, application of energy can be used to sever the specimen. That is, the vacuum can be used to suction the specimen into the cavity of the instrument, than energy can be applied to the tissue adjacent the specimen to sever the specimen. The specimen can then be aspirated through the elongated tube or maintained in the cavity. The suction cup can be used to raise and aspirate the specimen, e.g. the node, then resected with energy (or mechanically with a blade) and then energy applied to seal the tissue. This can include cautery to stop bleeding.

As seen in FIG. 12, it is also envisioned that each of these embodiments can be connected to a container 10, the container 10 including an elongate housing 12 having a lumen 14 defined therethrough and an aperture 16 disposed on the distal end thereof. The housing 12 has a bag 18 attached at the end thereof and disposed within the lumen 14, the bag 18 configured and dimensioned to helically encapsulate at least one specimen retracted by one of the foregoing dissection devices. This is advantageous in lymph node removal to prevent seeding.

It is also contemplated that visualization can be provided to identify the area proximate the surgical site. For example, CCD/DMOS VIZ chips at the head of the instrument to see the tissue in front or at a wider angle can be utilized.

The blades can have rigid or flexible tips to allow angled dissection in any direction.

It will be understood that various modifications may be made to the embodiments disclosed herein. Therefore, the above description should not be construed as limiting, but merely as an exemplification of the embodiments. Those skilled in the art will envision other modifications within the scope and spirit of the present disclosure. Such modification and variations are intended to come within the scope of the following claims.

What is claimed is:

1. A surgical device comprising:
a handle;
an elongated tube extending distally from the handle, the elongated tube defining a vacuum lumen therethrough;
a suction tip at a distal end portion of the elongated tube, the suction tip having an outwardly-facing, substantially hemispherical cavity formed therein with an open distal end, the vacuum lumen of the elongated tube opening into the cavity of the suction tip to facilitate application of a vacuum to the cavity; and
a C-shaped cutting blade having a first end directly, rotatably connected to the suction tip and a second end directly, rotatably connected to the suction tip, the cutting blade being positioned at least partially within the cavity and rotatable across the cavity to sever tissue, the cavity being dimensioned to receive tissue severed by the cutting blade to facilitate removal from a patient's body.

2. The device of claim 1, wherein the handle includes a manual member for rotating the cutting blade across the cavity.

3. The device of claim 2, wherein the manual member is operatively connected to an elongated actuator, the actuator being operatively connected to the cutting blade, wherein sliding movement of the manual member moves the actuator to rotate the cutting blade.

4. The surgical device of claim 3, wherein the actuator has a distal end fixedly connected to the cutting blade such that distal longitudinal movement of the actuator rotates the cutting blade.

5. The surgical device of claim 4, wherein the distal end of the actuator flexes in response to rotating the cutting blade.

6. The surgical device of claim 5, wherein the distal end of the actuator is fixedly connected to the cutting blade at a location adjacent the first end of the cutting blade.

7. The surgical device of claim 6, wherein the actuator defines a longitudinal axis, the distal end of the actuator extending laterally relative to the longitudinal axis of the actuator.

8. The device of claim 2, wherein the manual member includes a pivotable trigger, the trigger being operatively connected to an elongated actuator, the actuator being operatively connected to the cutting blade, wherein pivoting movement of the manual member moves the actuator to rotate the cutting blade.

9. The device of claim 2, wherein the manual member includes a plunger, the plunger being operatively connected to an elongated actuator, the actuator being operatively connected to the cutting blade, wherein sliding movement of the plunger moves the actuator to rotate the cutting blade.

10. The device of claim 2, further comprising an elongated rod operably associated with the manual member and the cutting blade to rotate the cutting blade.

11. The device of claim 1, wherein the cutting blade rotates across the cavity in an arc of about 180 degrees.

12. The device of claim 1, further comprising a rotatable knob for rotating the suction tip and the elongated tube about a longitudinal axis of the elongated tube.

13. The device of claim 1, wherein in an undeployed position of the cutting blade, the cutting blade is concealed within the cavity, and in a deployed position of the cutting blade, at least a portion of the cutting blade extends distally beyond the cavity.

14. The device of claim 13, wherein the cutting blade rotates across the cavity in an arc of about 180 degrees.

15. The device of claim 1, wherein at least one of the vacuum lumen and the cavity are configured and dimensioned to permit the passage of severed tissue therethrough upon the activation of the vacuum.

16. The device of claim 15, wherein the vacuum lumen is configured and dimensioned to draw severed tissue through both the cavity and the vacuum lumen upon the activation of the vacuum.

17. The device of claim 1, wherein the vacuum lumen and the cavity each define an axis therethrough that is disposed in alignment with a longitudinal axis extending through the elongated tube.

18. The device of claim 1, wherein the cavity increases in size from a proximal end of the cavity to the open distal end of the cavity such that the open distal end of the cavity is an enlarged opening.

19. A surgical device system comprising:
a surgical device, including:
a handle;
an elongated tube extending distally from the handle, the elongated tube defining a vacuum lumen therethrough;
a suction tip at a distal end portion of the elongated tube, the suction tip defining an outwardly-facing, substantially hemispherical cavity, the vacuum lumen of the elongated tube opening into the cavity of the suction tip to facilitate the application of a vacuum to the cavity; and
a C-shaped cutting blade having a first end directly, rotatably connected to the suction tip and a second end directly, rotatably connected to the suction tip, the cutting blade being positioned at least partially within the cavity and rotatable across the cavity to sever tissue, the cavity being configured and dimensioned to receive and maintain severed tissue therein upon activation of the vacuum; and
a container configured to receive the severed tissue upon deactivation of the vacuum.

20. The surgical device of claim 19, wherein a majority of a length of the cutting blade is flush with an inner surface of the suction tip.

21. The surgical device system of claim 19, wherein the cavity increases in size from a proximal end of the cavity to a distal end of the cavity such that the distal end of the cavity defines an enlarged opening.

22. A surgical device comprising:
   an elongated tube defining a vacuum lumen;
   a suction tip positioned adjacent a distal end portion of the elongated tube and defining a cavity, the vacuum lumen being in communication with the cavity to facilitate creation of a vacuum within the cavity; and
   a C-shaped cutting blade having a first end directly, rotatably connected to the suction tip and a second end directly, rotatably connected to the suction tip, the cavity being configured and dimensioned to receive tissue severed by the cutting blade to facilitate removal of the tissue from a patient's body, wherein the cutting blade is arcuate.

23. The surgical device of claim 22, wherein the cavity faces distally, and has a substantially hemispherical configuration.

24. The surgical device of claim 22, wherein the cutting blade is positioned at least partially within the cavity.

25. The surgical device of claim 24, wherein the cutting blade is movable between a first position, wherein the cutting blade is concealed within the cavity and a center point of the cutting blade is offset from a central longitudinal axis defined by the elongated tube, and a second position, wherein the cutting blade is at least partially exposed from the cavity and the center point of the cutting blade is disposed at the central longitudinal axis.

26. The surgical device of claim 22, wherein the cutting blade is rotatable about a fixed point.

* * * * *